US012502469B2

(12) United States Patent
Venkatachalapathy

(10) Patent No.: US 12,502,469 B2
(45) Date of Patent: Dec. 23, 2025

(54) AIR-POWERED PERITONEAL DIALYSIS SYSTEM WITH NESTING CONTAINERS

(71) Applicants: BAXTER INTERNATIONAL INC., Deerfield, IL (US); BAXTER HEALTHCARE SA, Glattpark (CH)

(72) Inventor: Narendar Venkatachalapathy, Karnataka (IN)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 471 days.

(21) Appl. No.: 18/020,189

(22) PCT Filed: Aug. 13, 2021

(86) PCT No.: PCT/US2021/045851
§ 371 (c)(1),
(2) Date: Feb. 7, 2023

(87) PCT Pub. No.: WO2022/040025
PCT Pub. Date: Feb. 24, 2022

(65) Prior Publication Data

US 2023/0293795 A1 Sep. 21, 2023

(30) Foreign Application Priority Data

Aug. 18, 2020 (IN) ............................ 202041035524

(51) Int. Cl.
*A61M 1/28* (2006.01)
*A61M 5/148* (2006.01)

(52) U.S. Cl.
CPC .......... *A61M 1/281* (2014.02); *A61M 5/1486* (2013.01); *A61M 5/1483* (2013.01);
(Continued)

(58) Field of Classification Search
CPC .. A61M 1/281; A61M 5/1486; A61M 5/1483; A61M 2205/07; A61M 2205/3334; A61M 2205/36; A61M 2205/3653
See application file for complete search history.

(56) References Cited

U.S. PATENT DOCUMENTS 5,720,728 A 2/1998 Dixon
7,559,913 B1 7/2009 Jeppsson et al.

FOREIGN PATENT DOCUMENTS

CN 107 837 432 3/2018
DE 600 35 615 11/2007

OTHER PUBLICATIONS

English translation Chinese Patent Publication No. 107837432 A (2018).*

(Continued)

*Primary Examiner* — John Kim
(74) *Attorney, Agent, or Firm* — K&L Gates LLP

(57) ABSTRACT

A peritoneal dialysis system comprises a cycler including an air pump; a heater housing including a heater and an expandable bladder in fluid communication with the air pump, wherein the heater housing is sized to receive a heater bag between a wall of the housing and the expandable bladder; a plurality of nesting containers configured for fluid communication with the air pump a disposable set operable with the cycler and including the heater bag and a plurality of fluid supply bags for placement within the plurality of nesting containers; and a control unit programmed to control the air pump and the heater.

17 Claims, 7 Drawing Sheets

(52) U.S. Cl.
CPC . *A61M 2205/07* (2013.01); *A61M 2205/3334* (2013.01); *A61M 2205/36* (2013.01); *A61M 2205/3653* (2013.01)

(56) References Cited

OTHER PUBLICATIONS

International Search Report, PCT/US2021/045851 mailing date Nov. 11, 2021—3 pages.
Written Opinion, PCT/US2021/0045851 mailing date Nov. 11, 2021—9 page.
EP Examination Report , Application No. 21 765 798.0-1113 mailed Jun. 12, 2025.

* cited by examiner

AIR-POWERED PERITONEAL DIALYSIS SYSTEM WITH NESTING CONTAINERS

PRIORITY CLAIM AND CROSS-REFERENCE TO RELATED APPLICATIONS

The present application is the National Stage filing under 35 U.S.C. § 371 of International Application No. PCT/US2021/045851, filed on Aug. 13, 2021, entitled "AIR-POWERED PERITONEAL DIALYSIS SYSTEM WITH NESTING CONTAINERS," which claims priority to and the benefit of Indian Provisional Application 20/204,1035524, filed Aug. 18, 2020, the entirety of which is herein incorporated by reference.

TECHNICAL FIELD

The present disclosure relates generally to medical fluid treatments and in particular to dialysis fluid treatments.

BACKGROUND

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal chamber. APD machines also allow for the dialysis fluid to dwell within the chamber and for the transfer of waste, toxins and excess water to take place. The source may include multiple liters of dialysis fluid including several solution bags.

APD machines pump used or spent dialysate from the peritoneal chamber, though the catheter, and to the drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

In any of the above modalities using an automated machine, the automated machine operates typically with a cycler programmed to control a cassette for pumping fluid between bags and to a patient. Programming the cycler to control the cassette's fluid pumping typically requires a complex logic circuit and complex pneumatic mechanisms. This complexity accordingly increases the costs associated with the cycler. Additionally, the cassette is typically part of a disposable set, which is discarded after a single use. Depending upon the complexity of the disposable set, the cost of using one set per day may become significant.

For each of the above reasons, it is desirable to provide a relatively simple APD machine, which operates a simple and cost effective disposable set.

SUMMARY

The present disclosure relates to an automated peritoneal dialysis ("APD") machine or cycler that drives fluid flow by way of air from an air pump. The APD machine or cycler includes nesting containers in fluid communication with an air pump. The nesting containers may be flexible, such as including a bag external to the APD machine or cycler, or rigid, such as a compartment within the APD machine or cycler's housing. The nesting containers are configured such that a bag filled with dialysis fluid may be positioned within a respective nesting container, either upon manufacture or after manufacture of the nesting container. With the fluid-filled bag positioned within the nesting container, the nesting container is filled with air to drive fluid out of the fluid-filled bag. For instance, when the system increases air pressure within the nesting container, an inward force is applied to the fluid-filled bag's exterior that drives fluid out of the fluid-filled bag. The nesting containers accordingly drive fluid flow from fluid supply bags during a dialysis treatment.

The presently disclosed APD machine or cycler also includes a heater housing. The heater housing in one embodiment includes a compartment for a bag or container filled with fluid, and a lid that closes over the compartment. The lid has an expandable bladder fixed to the lid's interior (or the bladder may be loosely located in or fixed to the compartment). The heater housing may also include a heater for heating the fluid in the bag or container positioned in the compartment. When the lid is closed, and the expandable bladder is inflated with air, the bladder and a compartment wall apply a compressive force to a heated, fluid-filled bag or container to drive heated fluid out of the bag or container. In an embodiment, the heater housing's expandable bladder may be inflated by the same air pump that provides air to the nested containers, e.g., via a pneumatic heater line. In an alternative embodiment, the heater housing's expandable bladder is inflated by a separate air pump. In such an alternative embodiment, the separate air pump may be a separate component connected to the cycler, integrated with the cycler or integrated with the heater housing.

The APD machine or cycler may be used with a disposable set for performing drain, fill and dwell cycles of a PD treatment. The disposable set may include fluid supply bags and fluid supply lines connected to each of the fluid supply bags. One of the fluid supply bags is a last fill bag in certain embodiments, wherein the dialysis solution has a different formulation than that of the other supply bags. In one embodiment, each of the fluid supply bags is positioned within a respective nesting container. The disposable set may also include a heater bag connected to a heater fluid line. The heater bag may be positioned within the heater housing. The disposable set may also include a drain bag connected to a drain fluid line, and may also include a patient fluid line for delivering fluid to and draining fluid from a patient. In one embodiment, the APD machine or cycler also includes a drain pump, e.g., a peristaltic pump in fluid communication with the drain line to drive fluid to the drain bag during a drain sequence. Each of the fluid lines may be in fluid communication with one another, for instance, by way of a disposable manifold.

The APD machine or cycler also includes a set of pneumatic lines to pneumatically connect each of the respective nesting containers and the heater housing's bladder to the one or more air pump. In an embodiment, the set of pneumatic lines is part of the disposable set. In another embodiment, the set of pneumatic lines is reusable. The pneumatic lines may fluidly communicate with one another, for instance, by way of a connector.

In an embodiment, the APD machine or cycler may include a set of valves or clamps, such as electrically actuated solenoid clamps, motorized punch valves or pneumatically actuated clamps, for (i) directing air flow from the air pump and (ii) directing fluid flow between the fluid bags and to and from the patient. The pneumatic supply lines, pneumatic heater line and pneumatic drain line may each be positioned within a clamp or operate with a pneumatic valve, such that when a respective clamp is closed, air cannot flow through the pneumatic line past the closed valve or clamp. In this way, the opened and closed valves or clamps on the pneumatic lines determine the path that air from the air pump takes. The fluid supply lines, heater fluid line, drain fluid line, and/or patient fluid line may each be positioned within a clamp such that when a respective clamp is closed, fluid cannot flow through the fluid line past the closed clamp. In this way, the opened and closed clamps on the fluid lines determine the path that fluid from the respective fluid bags or patient takes. The APD machine or cycler may also include a control unit programmed to control the air pump(s) and the clamps to direct the fluid flow from the fluid supply bags, heater bag and the patient during a drain, fill and dwell sequence. The APD machine or cycler of the present disclosure manages fluid flow by directing air flow to drive fluid out of the fluid-filled bags in the disposable set.

In one example sequence, the control unit is programmed to first execute a drain cycle. The clamps on the fluid supply lines and the heater fluid line are closed while the clamps on the drain fluid line and the patient line are opened. A drain, e.g., peristaltic, pump is then actuated to pull used dialysis fluid from the patient into the drain bag. After the drain cycle is complete, the clamps on the drain fluid line are closed. The heater housing's heater may heat the dialysis fluid in the heater bag during the drain cycle. The clamp and valve on the heater fluid line and the pneumatic heater line are then opened to begin a fill cycle. The remaining valves on the pneumatic lines are all closed. The air pump is actuated to inflate the heater housing's bladder and drive fluid from the heater bag into the patient. After a sufficient dwell time, another drain cycle is performed. The clamp and valve on the heater fluid line and pneumatic heater line are closed and the clamp on the drain fluid line is opened. The drain, e.g., peristaltic, pump is then actuated to drive fluid from the patient into the drain bag. After the drain cycle is complete, the clamps on the drain fluid line are closed.

The clamp and valve on a fluid supply line connected to a first supply bag and on a pneumatic supply line connected to the nesting container within which the first supply bag is positioned are then opened. The clamps on the heater fluid line are then opened. The air pump is then actuated to pump air, in a controlled manner, into the nesting container to drive fluid from the first supply bag to the heater bag. Once all or most of the fluid from the first fluid supply bag is transferred to the heater bag, the clamp and valve on the fluid supply line and pneumatic supply line are closed and the heater housing heats the fluid in the heater bag. The clamp on the heater fluid line may also be closed. The transfer of the fluid from the first supply bag to the heater bag may occur simultaneously with the directly preceding drain cycle.

After heating is complete, the clamps and valve on the heater fluid line, patient line and pneumatic heater line are opened. The air pump is actuated to inflate, in a controlled manner, the heater housing bladder. As the bladder inflates, it forces heated fluid out of the heater bag, through the heater fluid line and the patient line, to the patient. This example sequence may be repeated for each of the fluid supply bags positioned within their respective nesting containers.

It should be appreciated that because the air pressure in the nesting containers and the air-inflated bladder drives fluid flow, the APD machine or cycler of the present disclosure eliminates the need for a cassette to pump the fluid. The APD machine or cycler of the present disclosure therefore reduces the cost of a disposable set. The APD machine or cycler of the present disclosure additionally eliminates complex pneumatic mechanisms and complex logic present in other APD machines or cyclers operating with a rigid fluid cassette. Eliminating such complex pneumatic mechanisms and logic reduces the complexity and cost of the APD machine or cycler as of the present disclosure.

In light of the disclosure set forth herein, and without limiting the disclosure in any way, a peritoneal dialysis system includes: a cycler including an air pump, and a heater housing including a heater and an expandable bladder in pneumatic communication with the air pump, wherein the heater housing is sized to receive a heater bag between a wall of the housing and the expandable bladder; a plurality of nesting containers configured for pneumatic communication with the air pump; a disposable set operable with the cycler and including the heater bag and a plurality of fluid supply bags, each fluid supply bag of the plurality of fluid supply bags positioned within a respective nesting container of the plurality of nesting containers; and a control unit programmed to control the air pump and the heater.

In a second aspect, which may be used with any other aspect described herein, the control unit is programmed to cause the air pump to pump air to a first nesting container to push dialysis fluid from a first fluid supply bag positioned within the first nesting container.

In a third aspect, which may be used with any other aspect described herein, the peritoneal dialysis system is configured such that each nesting container may be inflated with air from the air pump independently of the other nesting containers.

In a fourth aspect, which may be used with any other aspect described herein, the peritoneal dialysis system is configured such that inflating the expandable bladder with air drives fluid out of the heater bag when positioned in the heater housing.

In a fifth aspect, which may be used with any other aspect described herein, the peritoneal dialysis system further includes a plurality of valves positioned to selectively control, via the control unit, air flow from the air pump to the plurality of nesting containers.

In a sixth aspect, which may be used with any other aspect described herein, the air pump is incorporated within the cycler.

In a seventh aspect, which may be used with any other aspect described herein, the control unit is configured to control a rate of fluid flow from one of the fluid supply bags by controlling the air pump.

In an eighth aspect, which may be used with any other aspect described herein, the peritoneal dialysis system includes at least one pressure sensor in pressure feedback communication with the control unit, the control unit configured to use the pressure feedback to control the air pump to not exceed at least one patient pressure limit.

In a ninth aspect, which may be used with any other aspect described herein, the disposable set further includes at least one of: the plurality of nesting containers, a drain bag, a supply line fluidly connected to each respective fluid supply bag, a heater line fluidly connected to the heater bag, and a drain line fluidly connected to the drain bag.

In a tenth aspect, which may be used with any other aspect described herein, the drain bag is positioned within a second nesting container, and wherein the drain bag is connected to the second nesting container such that expansion of the second nesting container causes expansion of the drain bag.

In an eleventh aspect, which may be used with any other aspect described herein, the peritoneal dialysis system is configured such that pumping air to the second nesting container creates a vacuum that pulls fluid from a patient to the drain bag.

In a twelfth aspect, which may be used with any other aspect described herein, the drain bag is ultrasonically welded or solvent bonded to the respective nesting container.

In a thirteenth aspect, which may be used with any other aspect described herein, the cycler further includes a drain pump positioned and arranged to deliver used dialysis fluid to the drain bag.

In a fourteenth aspect, which may be used with any other aspect described herein, the cycler further includes a plurality of fluid line clamps for selectively opening and occluding at least one of the supply lines, the heater line or the drain line.

In a fifteenth aspect, which may be used with any other aspect described herein, the peritoneal dialysis system includes a plurality of pneumatic lines in pneumatic communication with the air pump, the expandable bladder and the nesting containers.

In a sixteenth aspect, which may be used with any other aspect described herein, the pneumatic lines are reusable.

In a seventeenth aspect, which may be used with any other aspect described herein, the plurality of nesting containers are reusable or disposable.

In an eighteenth aspect, which may be used with any other aspect described herein, a peritoneal dialysis cycler includes: an air pump in pneumatic communication with a plurality of nesting containers and an expandable bladder; a heater housing including a heater and the expandable bladder located within the housing, the heater housing configured to receive a heater bag between a wall of the heater housing and the expandable bladder; a plurality of fluid line valves positioned and arranged to selectively open and occlude fresh and used dialysis fluid lines; a plurality of pneumatic valves positioned and arranged to selectively open and occlude a plurality of pneumatic lines; and a control unit programmed to control the air pump, the heater, at least one of the fluid line valves and at least one of the pneumatic valves to cause the heater bag to receive fresh dialysis fluid, the heater to heat the fresh dialysis fluid, and the air pump to expand the expandable bladder to push heated fresh dialysis fluid from the heater housing.

In a nineteenth aspect, which may be used with any other aspect described herein, the air pump, nesting containers, heater housing, fluid line valves, pneumatic valves and control unit are part of the cycler.

In a twentieth aspect, which may be used with any other aspect described herein, the heater housing is thermally insulated.

In a twenty-first aspect, which may be used with any other aspect described herein, the control unit is programmed to cause: fluid supply line valves and a heater fluid line valve to close, pneumatic supply line valves and a pneumatic heater line valve to close, the air pump to be actuated to provide air to a first nesting container having a drain bag within the first container, a drain fluid line valve to close, a pneumatic drain line valve to close, the heater fluid line valve to open, the pneumatic heater line valve to open, and the air pump to be actuated to inflate the expandable bladder.

In a twenty-second aspect, which may be used with any other aspect described herein, a peritoneal dialysis cycler includes: a cycler including an air pump, a drain pump, and a heater housing holding a heater and an expandable bladder, the expandable bladder in pneumatic communication with the air pump, wherein the heater housing is sized to receive a heater bag adjacent to the expandable bladder; a plurality of nesting containers configured for pneumatic communication with the air pump; a disposable set operable with the cycler and including the heater bag, a drain bag, and a plurality of fresh dialysis fluid supply bags, each fresh dialysis fluid supply bag positioned within one of the nesting containers; and a control unit programmed to control the air pump and the heater to pump heated fresh dialysis fluid from the cycler and the drain pump to pump used dialysis fluid to the drain container.

In a twenty-third aspect, any of the features, functionality and alternatives described in connection with any one or more of FIGS. 1 to 6B may be combined with any of the features, functionality and alternatives described in connection with any other of FIGS. 1 to 6B.

It is accordingly an advantage of the present disclosure to provide an APD system that uses a low cost and simple cycler and a low cost and simple disposable.

It is another advantage of the present disclosure to provide an APD system that eliminates the need for a cassette.

It is a further advantage of the present disclosure to provide an APD system that eliminates the complex pneumatic mechanism for pumping fluid using a cassette.

It is still another advantage of the present disclosure to provide an APD system that eliminates the complex logic circuit required for pumping fluid using a cassette.

It is yet another advantage of the present disclosure to provide an APD system that simplifies the logic circuit required to move fluid between fluid bags and to and from the patient.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1:
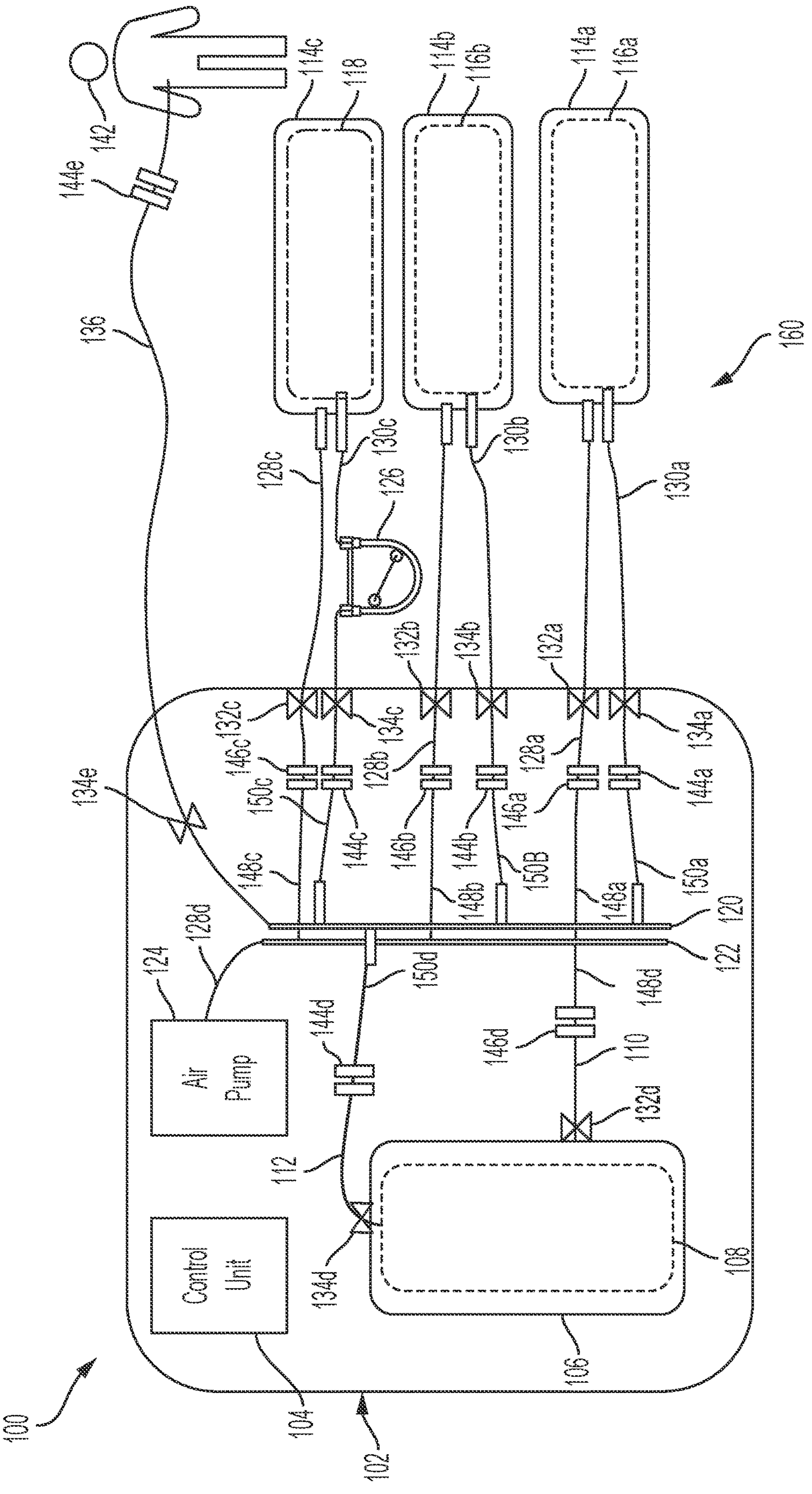
FIG. 1 illustrates an example peritoneal dialysis system of the present disclosure.

Referring now to the drawings and in particular to FIG. 1, a peritoneal dialysis ("PD") system 100 includes a PD cycler 102 that operates with a set of nesting containers 114*a*, 114*b*, 114*c* and a disposable set 160, which may or may not include nesting containers 114*a*, 114*b*, 114*c*. In an embodiment, PD cycler 102 includes a heater housing 106, an air pump 124 and a control unit 104. Heater housing 106 includes a compartment and a lid that may enclose the compartment. An expandable bladder is fixed to an interior of the lid of heater housing (the bladder is alternatively fixed to the compartment or placed in the compartment). The heater housing 106 is explained in more detail in connection with FIGS. 3A, 3B, 4A and 4B. PD cycler 102 may also include a housing that contains each of the components of PD cycler 102. The housing, in some embodiments, may be constructed of one or more plastic, such as, polyvinyl chloride ("PVC"), polyethylene ("PE") or polyurethane ("PU"), or other suitable non-PVC polymer. In other embodiments, the housing may additionally or alternatively be constructed of a metal or metal alloy, such as aluminum, steel or stainless steel and alloys thereof.

The disposable set 160 of PD system 100 may include multiple fluid supply bags 114*a*, 114*b* (e.g., two, three or more supply bags). Each of the respective fluid supply bags 116*a*, 116*b* is positioned within respective nesting containers 114*a*, 114*b*. For instance, fluid supply bag 116*a* is positioned within nesting container 114*a*, while fluid supply bag 116*b* is positioned within nesting container 114*b*. The fluid supply bags 116*a*, 116*b* may be filled with premade dialysis fluid. In some embodiments, one of the fluid supply bags 116*a*, 116*b* is a premixed last fill bag of dialysis fluid having a different formulation tailored for an extended dwell. The disposable set 160 also includes fluid supply lines 130*a*, 130*b*. Fluid supply line 130*a* extends from fluid supply bag 116*a* and terminates at fluid supply line connector 144*a*. Fluid supply line 130*b* extends from fluid supply bag 116*b* and terminates at fluid supply line connector 144*b*.

In embodiments in which there are more than two fluid supply bags 116*a*, 116*b* (e.g., three), fluid supply line 130*a* or 130*b* may branch off to the additional fluid supply bag. For example, if fluid supply bag 116*b* is a last fill bag and fluid supply bag 116*a* is a supply bag for a fill, dwell and drain sequence, fluid supply line 130*a* may branch off to the additional fluid supply bag because it is not a last fill bag. In other examples, the additional supply bag may have its own fluid supply line rather than a branching off section from fluid supply lines 130*a* or 130*b*.

The disposable set 160 of the PD system 100 also includes a heater bag 108. The heater bag 108 is positioned within the compartment of the heater housing 106. When placed in the compartment of the heater housing 106, the heater bag 108 may be pre-filled with dialysis fluid or may be empty. The disposable set 160 also includes a heater fluid line 112 that extends from the heater bag 108 and terminates at a heater fluid line connector 144*d*. The disposable set 160 further includes a drain bag 118. The drain bag 118 may collect fluid drained from a patient 142. The disposable set 160 also includes a drain fluid line 130*c* that extends from the drain bag 118 and terminates at a drain line connector 144*c*. In some embodiments, the PD system 100 may include a drain pump 126, such as a peristaltic, gear or membrane pump, in fluid communication with drain fluid line 130*c* for removing dialysis fluid from patient 142 to drain bag 118.

PD system 100 is configured such that fluid supply lines 130*a*, 130*b*, heater fluid line 112, drain line 130*c*, and a patient line 136 are in fluid communication with one another. Fluidly connecting each of the respective lines enables fluid to be transferred between fluid bags (e.g., between supply bag 116*a* and heater bag 108) and between a fluid bag and patient 142 (e.g., between heater bag 108 and patient 142). For example, a fluid line connector 120 may include connecting tubes and line connectors to fluidly connect each of the fluid lines. Fluid line connector 120 may include a connecting tube 150*a* terminating at supply connector 144*a*, and a connecting tube 150*b* terminating at supply connector 144*b*. In certain embodiments, fluid line connector 120 may include an additional connecting tube and connector for instances in which there are more than two fluid supply bags 116*a*, 116*b*. Fluid line connector 120 may also include a connecting tube 150*c* terminating at drain connector 144*c*. Fluid line connector 120 may further include a connecting tube 150*d* terminating at heater connector 144*d*. Fluid line connector 120 may also include patient line 136 terminating at a patient connector 144*e*.

All components of the disposable set 160, including all fluid lines, fluid bags or containers and fluid line connectors may be made of any one or more plastic, such as, polyvinyl chloride ("PVC"), polyethylene ("PE") or polyurethane ("PU"), or other suitable non-PVC polymer.

PD system 100 is configured to direct fluid flow. For example, PD system 100 may include a set of clamps or valves that are positioned on the fluid lines or connecting tubes of fluid line connector 120 to control fluid flow through the fluid lines. Closing and opening desired clamps or valves directs where fluid flows within system 100, such as from fluid supply bag 116*a* to heater bag 108. In the illustrated embodiment, clamp 134*a* is positioned on connecting tube 150*a*, clamp 134*b* is positioned on connecting tube 150*b*, clamp 134*c* is positioned on connecting tube 150*c*, clamp 134*d* is positioned on connecting tube 150*d*, and clamp 134*e* is positioned on patient line 136.

In various embodiments, clamps 134*a*, 134*b*, 134*c*, 134*d* and 134*e* may be electrically actuated solenoid valves, motorized pinch clamps, or pneumatically actuated valves or clamps. In one embodiment, valves or clamps 134*a*, 134*b*, 134*c*, 134*d* and/or 134*e* are solenoid valves or variable orifice valves. In another embodiment, valves or clamps 134*a*, 134*b*, 134*c*, 134*d* and/or 134*e* are clamps that are manually opened and closed. In some embodiments, a portion of valves or clamps 134*a*, 134*b*, 134*c*, 134*d* and/or 134*e* are automatic valves, while a remaining portion are manual clamps. When in an open position, valve or clamp 134*a*, 134*b*, 134*c*, 134*d* or 134*e* enables fresh or used dialysis fluid to flow through a fluid line or connecting tube. When in a closed position, valve or clamp 134*a*, 134*b*, 134*c*, 134*d* or 134*e* prevents fresh or used dialysis fluid from flowing through a fluid line or connecting tube past the closed valve or clamp 134*a*, 134*b*, 134*c*, 134*d* or 134*e*. Automatic valves 134*a*, 134*b*, 134*c*, 134*d* and 134*e* are controlled by a control unit in various embodiments. Flowrate and pressure control are performed via the control unit and pumps of the present disclosure as discussed below.

In some example embodiments, valves or clamps 134*a*, 134*b*, 134*c*, 134*d* and 134*e* may be separate components added to the fluid lines. In other embodiments, clamps or valves 134*a*, 134*b*, 134*c*, 134*d* and 134*e* are integrated with PD cycler 102, such as being fixed to the interior or exterior of a housing of PD cycler 102. In such embodiments, patient line 136 and connecting tubes 150*a*, 150*b*, 150*c* and/or 150*d* may be positioned within respective clamps or valves 134*a*, 134*b*, 134*c*, 134*d* and/or 134*e* in preparation for one or more drain, fill, dwell cycles with the APD machine or cycler. Additionally or alternatively, lines 130*a*, 130*b*, 130*c*, 112 and/or 136 may be positioned within respective clamps or valves 134*a*, 134*b*, 134*c*, 134*d* and/or 134*e*. In the illustrated embodiment, valves 134*a*, 134*b*, 134*c*, 134*d* and 134*e* are integrated within an interior of the housing of the PD cycler 102 at various positions. In other embodiments, valves 134*a*, 134*b*, 134*c*, 134*d* and 134*e* are positioned along an exterior of the housing of PD cycler 102, through which the fluid lines are extended.

PD system 100 also includes a set of pneumatic lines in fluid communication with air pump 124. In some embodiments, the pneumatic lines are included as part of the disposable set 160, and therefore may be disposed of after a certain quantity of uses. In other embodiments, the pneumatic lines are reusable components. For example, the pneumatic lines may be integrated with PD cycler 102 or may be separate components that are reusable. In certain embodiments, the pneumatic lines may be made of any one or more plastic, such as, polyvinyl chloride ("PVC"), polyethylene ("PE") or polyurethane ("PU"), or other suitable non-PVC polymer. The pneumatic lines are alternatively metal, e.g., stainless steel. FIG. 1 illustrates that a pneumatic supply line 128*a* extends from nesting container 114*a* and terminates at supply connector 146*a*. A pneumatic supply line 128*b* extends from nesting container 114*b* and terminates at supply connector 146*b*. A pneumatic drain line 128*c* extends from nesting container 114*c* and terminates at drain connector 146*c*. A pneumatic heater line 110 extends from heater housing 106 and terminates at heater connector 146*d*. Pneumatic heater line 110 is in fluid communication with the expandable bladder of heater housing 106, as described in more detail below.

In the illustrated embodiment, pneumatic supply lines 128*a*, 128*b*, pneumatic drain line 128*c*, and pneumatic heater line 110 are in fluid communication with air pump 124 by way of a pneumatic line connector 122. Air pump 124 is connected directly to pneumatic line connector 122 via pneumatic pump line 128*d*. In other embodiments, pneumatic pump line 128*d* may be connected to pneumatic line connector 122 via a line connector. Fluidly connecting each of the pneumatic lines to air pump 124 enables air pump 124 to deliver air to each of the respective nesting containers and to the expandable bladder of heater housing 106. Pneumatic line connector 122 may include connecting tubes and line connectors to fluidly connect each of the pneumatic lines. Pneumatic line connector 122 may include a connecting tube 148*a* terminating at supply connector 146*a*, and a connecting tube 148*b* terminating at supply connector 146*b*. In certain embodiments, pneumatic line connector 122 may include an additional connecting tube and connector for instances in which there are additional nesting containers 114*a*, 114*b*, e.g., instances in which there are more than two fluid supply bags 116*a*, 116*b*. Pneumatic line connector 122 may also include a connecting tube 148*c* terminating at drain connector 146*c*. Pneumatic line connector 122 may also include a connecting tube 148*d* terminating at heater connector 146*d*.

In certain embodiments, air pump 124 is integrated within a housing of PD cycler 102. In other embodiments, air pump 124 is a separate component from PD cycler 102 and is pneumatically connected to PD cycler 102. FIG. 1 illustrates PD cycler 102 having a single air pump 124. In other embodiments, PD cycler 102 may have more than one air pump 124. For instance, PD cycler 102 may include a first air pump in fluid communication with the respective nesting containers and a second air pump in fluid communication with the bladder of heater housing 106. In another instance, PD cycler 102 includes a respective air pump for each respective nesting container, and a separate air pump for the bladder of heater housing 106.

PD system 100 is configured such that the direction of air flow from air pump 124 may be controlled within PD system 100. For example, PD system 100 may include a set of clamps or valves that are positioned on the pneumatic lines or connecting tubes of pneumatic line connector 122 to control air flow through the pneumatic lines. For example, valve 132*a* is positioned on connecting tube 148*a*, valve 132*b* is positioned on connecting tube 148*b*, valve 132*c* is positioned on connecting tube 148*c*, and valve 132*d* is positioned on connecting tube 148*d*.

In various embodiments, valves 132*a*, 132*b*, 132*c* and 132*d* may be electrically actuated solenoid valves or clamps or pneumatically actuated valves or clamps. In one embodiment, valves 132*a*, 132*b*, 132*c* and/or 132*d* are solenoid or variable orifice valves. In another embodiment, valves 132*a*, 132*b*, 132*c* and/or 132*d* are clamps that are manually opened and closed. In some embodiments, a portion of valves 132*a*, 132*b*, 132*c* and 132*d* are automatic valves, while a remaining portion are manually operated clamps. When in an open position, valves 132*a*, 132*b*, 132*c* and 132*d* enable air to flow through a pneumatic line or connecting tube. When in a closed position, valves 132*a*, 132*b*, 132*c* and 132*d* prevent air from flowing through a pneumatic line or connecting tube past the closed valve 132*a*, 132*b*, 132*c* and 132*d*. Valves 132*a*, 132*b*, 132*c* and 132*d* may be controlled by a control unit in various embodiments. The valves control direction while the pneumatic pump controls pneumatic pressure and flow.

In some example embodiments, valves 132*a*, 132*b*, 132*c* and 132*d* may be separate components added to the pneumatic lines. In other embodiments, valves 132*a*, 132*b*, 132*c* and 132*d* may be integrated with PD cycler 102, such as being fixed to the interior of a housing of PD cycler 102. In such embodiments, connectors 146*a*, 146*b*, 146*c* and/or 146*d* may be positioned within respective valves 132*a*, 132*b*, 132*c* and/or 132*d* in preparation for one or more drain, fill, dwell cycles with the APD machine or cycler. Additionally or alternatively, the lines 128*a*, 128*b*, 128*c* and/or 110 may be positioned within respective valves 132*a*, 132*b*, 132*c* and/or 132*d*. In the illustrated embodiment, the valves 132*a*, 132*b*, 132*c* and 132*d* are integrated with an interior of the housing of the PD cycler 102 at various positions. In other embodiments, the valves 132*a*, 132*b*, 132*c* and 132*d* may each respectively be positioned along an exterior of a housing of the PD cycler 102 through which the pneumatic supply and drain lines extend and exit the PD cycler 102.

In various embodiments, PD cycler 102 may also include a control unit 104 that is communicatively coupled to the components discussed herein, though such connections are not shown for clarity. For instance, the control unit 104 is programmed to control valves or clamps 132*a*, 132*b*, 132*c*, 132*d*, 134*a*, 134*b*, 134*c*, 134*d* and 134*e*, air pump 124 and drain pump 126 to drive and direct fluid flow in PD system 100. Control unit 104 includes at least one processor and at least one memory in communication with the at least one processor. Control unit 104 may be stored within the housing of PD cycler 102. Control unit 104, in some instances, also includes a wired or wireless transceiver for sending information to and receiving information from an external device. Wired communication may be via Ethernet connection, for example. Wireless communication may be performed via any of Bluetooth™, WiFi™, Zigbee®, Z-Wave®, wireless Universal Serial Bus ("USB"), or infrared protocols, or via any other suitable wireless communication technology. Example programming logic stored in the memory of control unit 104 and executed by the processor of control unit 104 will be discussed in more detail below.

PD cycler 102 may also include a user interface (not illustrated). For example, the user interface may be integrated with a housing of the PD cycler 102. Control unit 104 in an embodiment includes a video controller, which may have its own processing and memory for interacting with primary control processing and memory of control unit 104. The user interface may include a video monitor, which may operate with a touch screen overlay placed onto the video monitor for inputting commands into control unit 104. The user interface may also include one or more electromechanical input device, such as a membrane switch or other button. Control unit 104 may further include an audio controller for playing sound files, such as alarms and/or voice activation commands, at one or more speaker of the user interface.

Figure 2A:
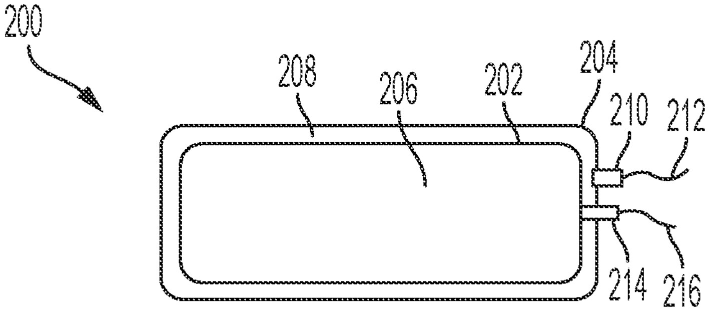
FIGS. 2A and 2B illustrate an example fluid supply bag configuration including a fluid supply bag positioned within a nesting container, according to an aspect of the present disclosure.
Figure 2B:
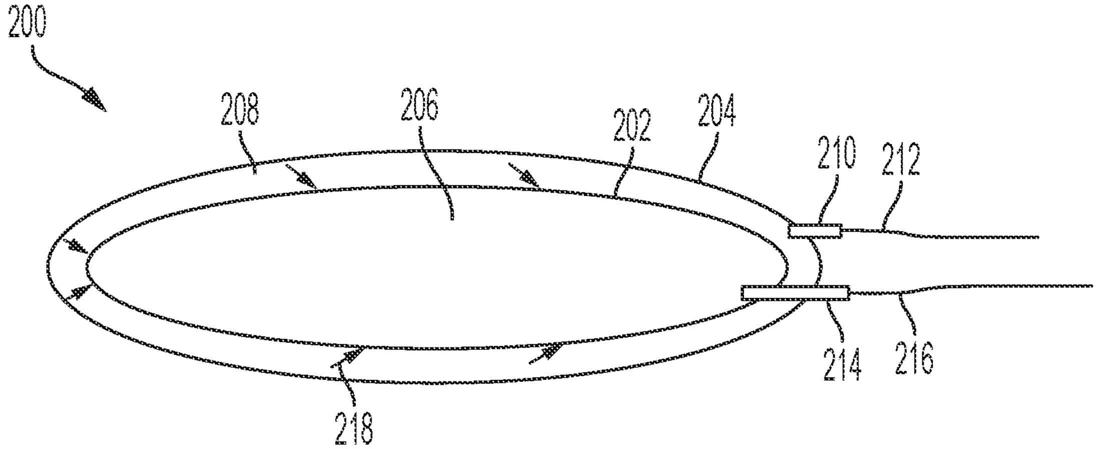

FIGS. 2A and 2B illustrate an example fluid supply bag configuration 200 with a fluid supply bag 202 positioned within a nesting container 204 to show the mechanism by which air from air pump 124 drives fluid flow in PD system 100. FIG. 2A, in particular, illustrates a top view of fluid supply bag configuration 200. Fluid supply bag 202 includes a fluid outlet 214 in fluid communication with a fluid line 216 and a fluid supply bag interior 206. Nesting container 204 includes an air inlet 210 in fluid communication with a pneumatic line 212 and a nesting bag interior 208. As illustrated, nesting bag interior 208 constitutes the space within nesting container 204 that is external to fluid supply bag 202. In some embodiments, nesting container 204 may be flexible, such as a flexible bag that can fold flat in a deflated state and inflate with air to a maximum interior volume. In other embodiments, nesting container 204 may be rigid, such as a rigid chamber. In various embodiments, nesting container 204 may be made of any one or more plastic, such as, polyvinyl chloride ("PVC"), polyethylene ("PE") or polyurethane ("PU"), or other suitable non-PVC polymer. In other embodiments, nesting container 204 may be made of any one or more metal or metal alloy. The nesting container 204 may be disposable or may be reusable. For instance, the nesting container 204 may be integrated with a disposable fluid supply bag 202 such that the whole construct is disposable. In other instances, the nesting container 204 may be a separate component from the fluid supply bag 202 and therefore may be reused irrespective of whether the fluid supply bag 202 is disposable.

In certain embodiments, such as the one illustrated, fluid supply bag configuration 200 includes interfaces between (i) fluid outlet 214 and fluid supply bag 202, (ii) fluid outlet 214 and nesting container 204 and (iii) air inlet 210 and nesting container 204. In such embodiments, the interfaces are airtight. For instance, the interfaces may be sealed during manufacture. The seals prevent fluid within fluid supply bag 202 from entering nesting container interior 208 and prevent air from entering fluid supply bag 202. The seals also ensure that nesting container 204 is airtight so that air introduced into nesting container interior 208 does not escape. This enables air pressure to build within nesting container interior 208 as air is introduced (e.g., by an air pump).

In other embodiments, fluid supply bag configuration 200 does not include one or both of such interfaces. For example, air inlet 210 may be formed integrally with nesting container 204 instead of being a separate component. In another example, fluid outlet 214 may be formed integrally with both fluid supply bag 202 and nesting container 204.

FIG. 2B illustrates a cross-sectional side view of fluid supply bag configuration 200. As air is introduced (e.g., by an air pump) into nesting container interior 208, air pressure within closed volume nesting container interior 208 increases. For example, in instances in which nesting container 204 is flexible, the introduced air inflates nesting container 204 to its maximum interior volume and further introduced air increases the interior air pressure because the interior volume of nesting container 204 remains constant. In another example, in instances in which nesting container 204 is rigid, the interior volume of the rigid nesting container 204 remains constant and therefore the introduced air increases the interior air pressure. The air pressure within nesting container interior 208 applies inward force to fluid supply bag 202 in the direction of arrows 218. It should be appreciated that only one arrow is indicated in FIG. 2B for the sake of clarity. The inward force applied to fluid supply bag 202 from the air pressure drives fluid out of fluid supply bag 202 and through fluid outlet 214 and fluid supply line 216. The rate at which fluid exits fluid supply bag 202 is dependent upon the rate at which air is introduced into nesting container 204. For instance, the greater the air flow rate into nesting container 204, the faster the interior air pressure increases, and the faster the air pressure drives the fluid out of fluid supply bag 202.

Figure 3A:
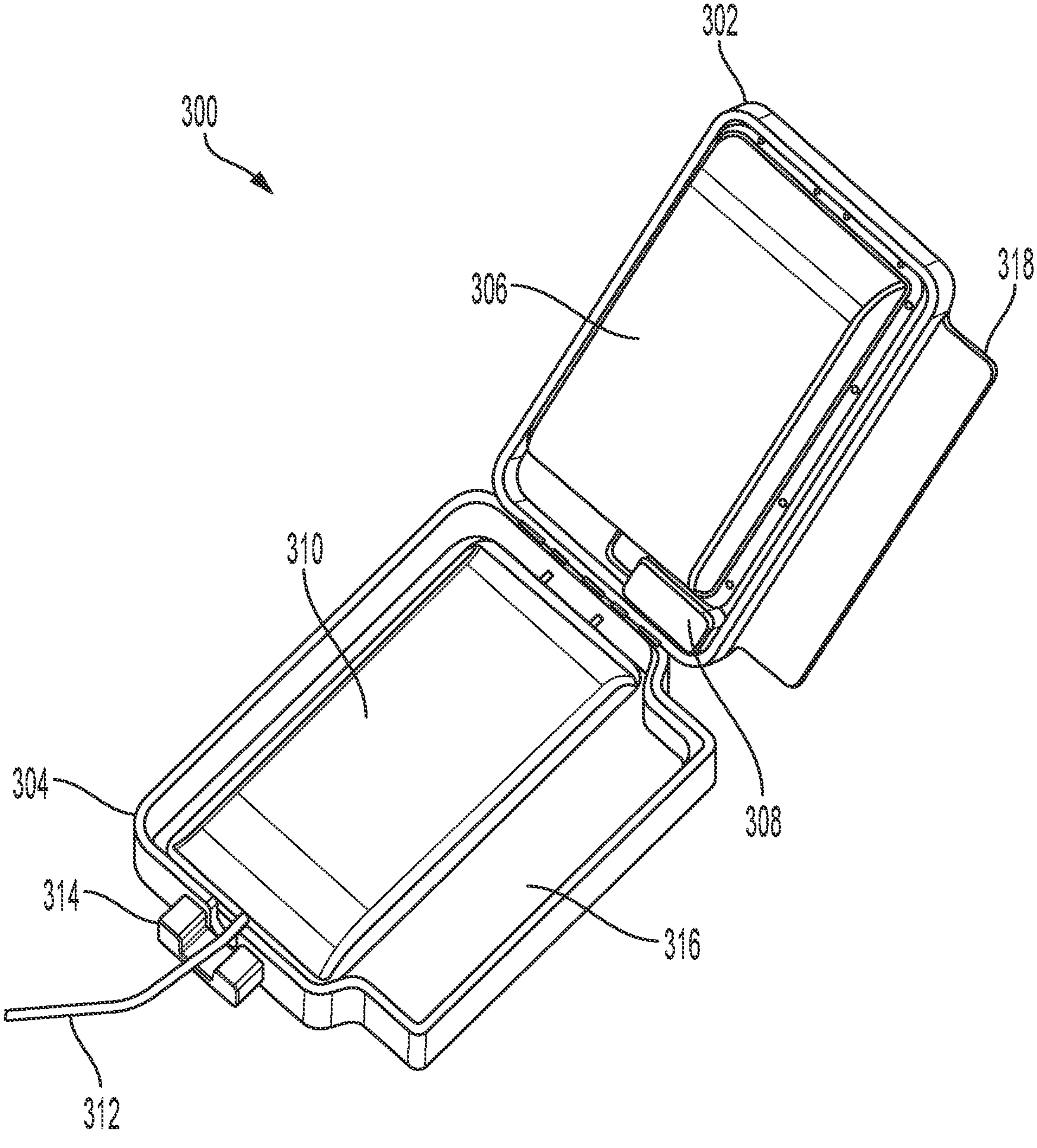
FIGS. 3A and 3B illustrate an example heater housing, according to an aspect of the present disclosure.
Figure 3B:
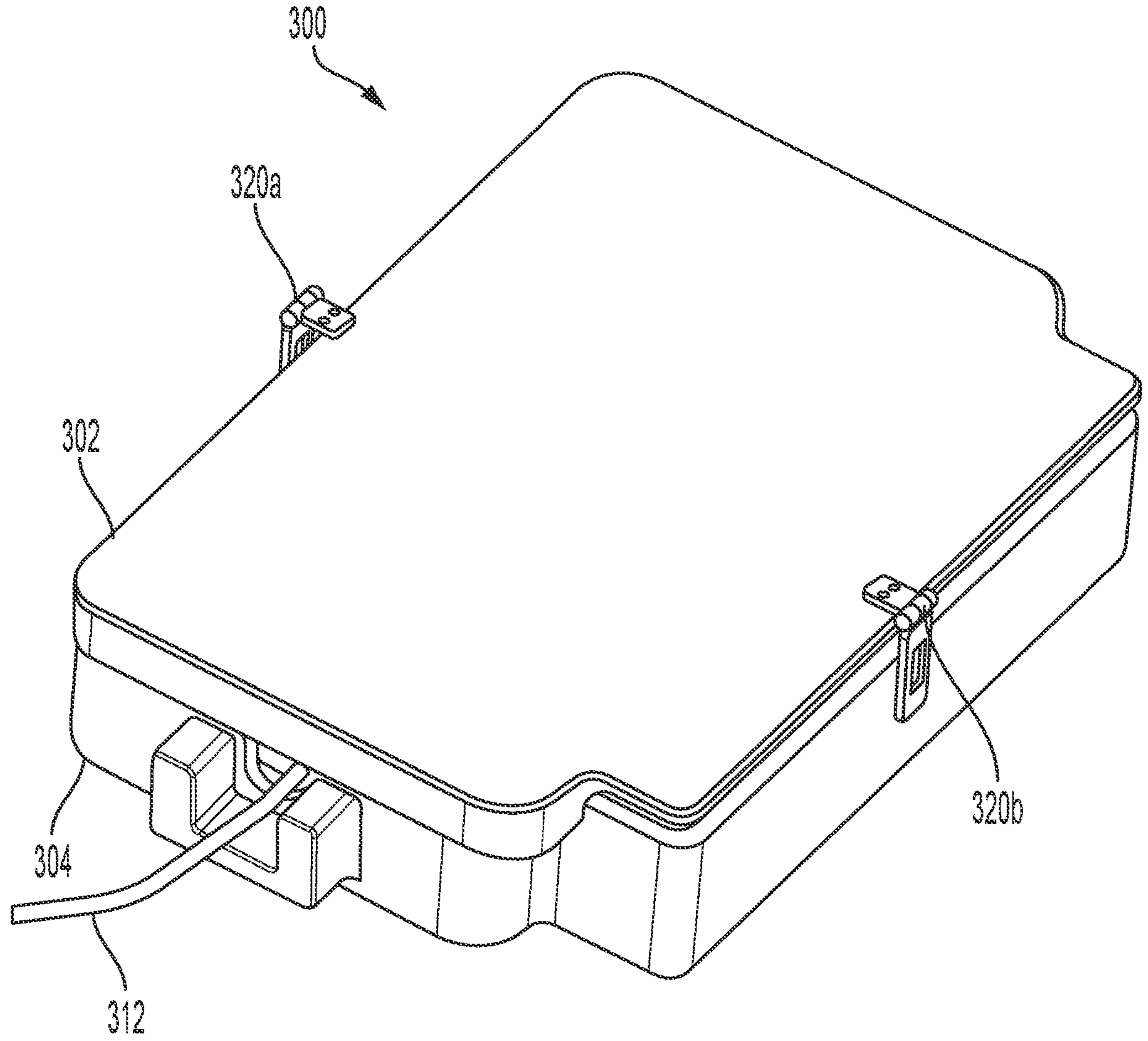

FIGS. 3A and 3B illustrate an example heater housing 300 in an open and closed position, respectively. In certain embodiments (e.g., FIG. 1), heater housing 300 is integrated with the housing of the presently disclosed PD cycler. In at least one embodiment, heater housing 300 may be a component separate from the PD cycler. Heater housing 300 includes a lid 302 and a compartment 304. Lid 302 may be connected to compartment 304, for example by a hinge, such that lid 302 may be closed over compartment 304. When the lid 302 is closed, heater housing 300 is thermally insulated in one embodiment.

The heater housing 300 includes an expandable bladder 306. In some embodiments, the expandable bladder 306 is attached to the interior of the heater housing 300, such as to the interior of lid 302. In other embodiments, the expandable bladder 306 is instead fitted within a holding section in the interior of the heater housing 300 rather than being attached to the heater housing 300. Bladder 306 may be constructed of rubber, e.g., silicone rubber, PVC-type flexible plastic material, or other material of suitable strength and flexibility to repeatedly expand and contract over many cycles. In some instances, bladder 306 may be fixedly attached to the interior of lid 302, for example, by adhesive. In other instances, bladder 306 may be removably attached to the interior of lid 302, for example, by hook and loop fasteners (e.g., Velcro®), snap components, hanging on hooks, or other suitable temporary attachment mechanisms. Removably attaching the bladder 306 to the interior of lid 302 may enable easier maintenance of heater housing 300. For example, if bladder 306 ruptures it may easily be replaced without replacing any other components of heater housing 300. Bladder 306 may include flanges for removable attachment. Bladder 306 is alternatively loosely or fixedly located within the compartment of heater housing 300.

In various embodiments, bladder 306 is in fluid communication with an air pump 308 integrated in the presently disclosed PD cycler. Additionally or alternatively, heater housing 300 may include an air pump 308 integrated with lid 302. Air pump 308 is fluidly connected to bladder 306 to inflate bladder 306 with air. Batteries or an external power supply may provide air pump 308 with necessary power to pump air into bladder 306.

Compartment 304 is configured such that a bag or container filled with fluid may be positioned within compartment 304. For example, FIG. 3A illustrates a fluid bag or container 310 positioned within compartment 304. Fluid bag or container 310 includes a fluid outlet 312. Heater housing 300 may also include a heater (not illustrated) to heat the fluid in fluid bag or container 310. For example, the heater may be located inside compartment 304 (e.g., below fluid bag or container 310 in the illustrated embodiment) and in an embodiment includes heating coils that contact a heating pan, which is located at the bottom of compartment 304. Heating may be resistive, inductive, infrared and combinations thereof. Compartment 304 includes an example opening 314 such that fluid outlet 312 is external to heater housing 300 when heater housing 300 is closed with fluid bag or container 310 positioned inside. In various embodiments, compartment 304 may include a storage area 316. Storage area 316 may provide an empty space for placing various items. For example, a disposable set 160 and/or clamps or valves may be stored in the storage area 316 between dialysis sessions or during a dialysis session. In embodiments in which clamps or valves are integrated with the PD cycler, as described above, the clamps or valves may be integrated with heater housing 300 in storage area 316. Lid 302 may also include an extension 318 configured to cover storage area 316 when lid 302 is in a closed position.

FIG. 3B illustrates example heater housing 300 in a closed configuration with fluid bag or container 310 positioned inside. Lid 302 is illustrated in a closed position over compartment 304 and fluid outlet 312 is shown external to heater housing 300. Heater housing 300 additionally includes a mechanism to maintain lid 302 in a closed position relative to compartment 304. For instance, as bladder 306 is inflated with air and expands it will push lid 302 open unless lid 302 is maintained in the closed position. Bladder 306 would also not apply sufficient compressive force to fluid bag or container 310 to drive fluid out of fluid bag or container 310 if lid 302 were to open as bladder 306 expands (e.g., see FIGS. 4A and 4B). In various embodiments, heater housing 300 includes holding clamps 320*a* and 320*b*. Holding clamps 320*a* and 320*b* may be attached to an outer surface of compartment 304 and may be adjusted so that the clamps are positioned to maintain lid 302 in a closed position against the force applied to lid 302 by the expanding bladder 306. Holding clamps 320*a* and 320*b* may also be adjusted so that lid 302 may be opened. In other embodiments, heater housing 300 may include other suitable mechanisms for maintaining lid 302 in a closed positioned, such as a snap mechanism in which lid 302 or compartment 304 includes a notch and the other includes a protrusion.

Figure 4A:
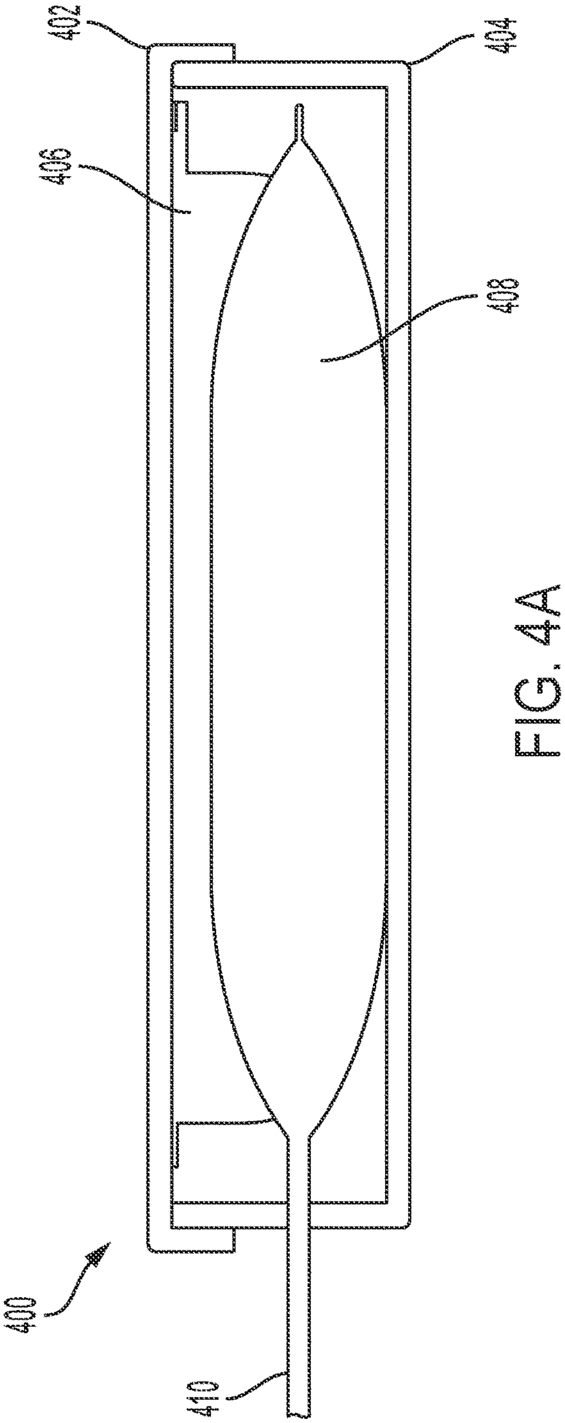
FIG. 4A illustrates a cross-sectional side view of an example heater housing showing a bladder in a deflated condition, according to an aspect of the present disclosure.
Figure 4B:
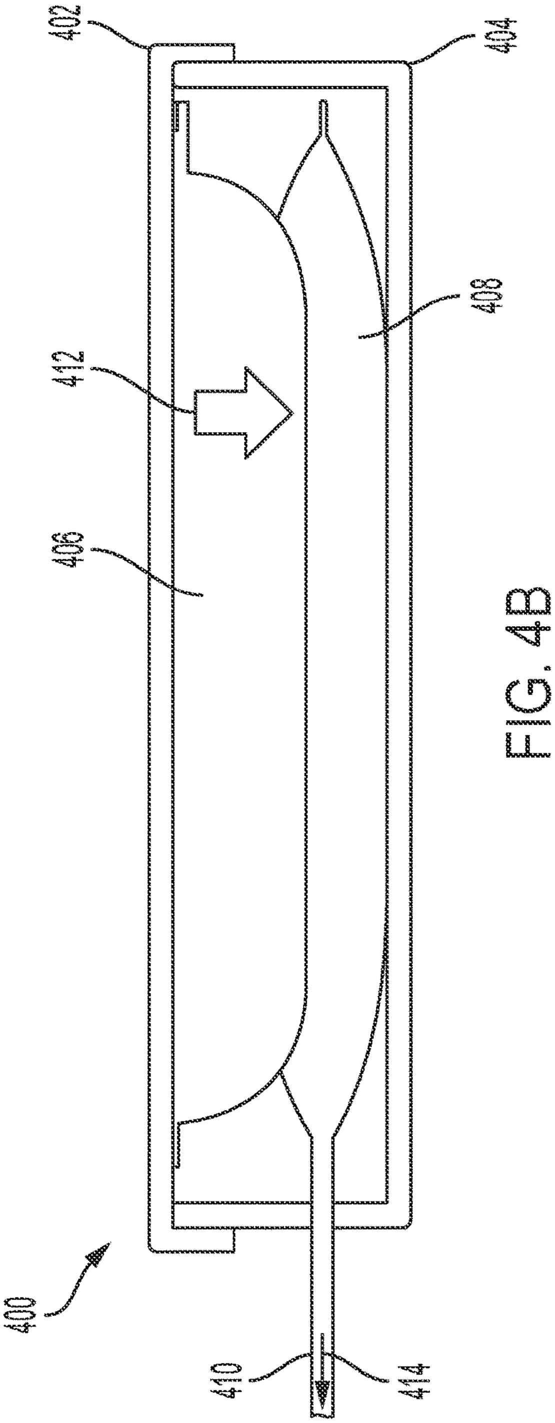
FIG. 4B illustrates a cross-sectional side view of an example heater housing showing an inflated bladder forcing fluid from a heater bag, according to an aspect of the present disclosure.

FIGS. 4A and 4B illustrate a cross-sectional side view of an example heater housing 400 in a closed configuration to show the heater housing fluid-driving mechanism. Heater housing 400 includes a lid 402, a compartment 404 and a bladder 406. A fluid bag or container 408 filled with dialysis fluid is positioned within compartment 404. Fluid bag or container 408 includes a fluid outlet 410. FIG. 4A illustrates bladder 406 in a deflated condition and fluid bag or container 408 in a full state. Bladder 406 may then be inflated with air in a controlled manner, causing bladder 406 to expand away from lid 402 in the direction of arrow 412. FIG. 4B illustrates bladder 406 in a partially inflated condition and fluid bag or container 408 in a partially emptied state. As bladder 406 is inflated with air and expands, bladder 406 and compartment 404 apply compressive force to fluid bag or container 408, which drives fluid out of fluid bag or container 408 through fluid outlet 410 in the direction of arrow 414. Bladder 406 may be inflated with air until all or most of the fluid is driven out of fluid bag or container 408. The rate at which fluid exits fluid bag or container 408 is dependent upon the rate at which air is introduced into bladder 406. For instance, the greater the air flow rate into bladder 406, the faster bladder 406 expands, and the faster the generated compressive force drives the fluid out of fluid bag or container 408.

Returning to FIG. 1, PD cycler 102 in the illustrated embodiment includes a control unit 104 programmed to control air pump 124, pump 126 and valves and clamps 132*a*, 132*b*, 132*c*, 132*d*, 134*a*, 134*b*, 134*c*, 134*d* and 134*e* to direct air flow and fluid flow in PD system 100. For instance, control unit 104 is programmed to control air pump 124 and valves 132*a*, 132*b*, 132*c* and 132*d* to direct air flow to nesting container 114*a*, nesting container 114*b*, nesting container 114*c* or the bladder in heater housing 106. By way of the air-based fluid driving mechanisms described above, control unit 104 is also programmed to control pump 126 and clamps 134*a*, 134*b*, 134*c*, 134*d* and 134*e* to direct fluid flow between (i) respective supply bags 116A, 116B and heater bag 108, (ii) heater bag 108 and patient 142, and (iii) patient 142 and drain bag 118. While the fresh dialysis fluid is premade and bagged in the illustrated embodiment, control unit 104 may alternatively be programmed to prepare fresh dialysis solution at the point of use, cause the solution to mix, e.g., within an accumulator bag or heater bag 108, drive the freshly prepared dialysis fluid from the accumulator bag or heater bag 108 to patient 142, allow the dialysis fluid to dwell within patient 142, then pump used dialysis fluid to drain bag 118. Control unit 104 may also be programmed to control the heater of heater housing 106.

In one example, control unit 104 is programmed to execute the following sequence assuming that each respective clamp and valve in PD system 100 begins in an open state. For instance, the sequence may begin upon a user initiating the sequence from the user interface of the PD cycler 102. Additionally, heater bag 108 is full at the start of the example sequence. In the example, a drain cycle is first conducted. Clamps 134*a*, 134*b* and 134*d* are closed. Clamps 134*c* and 134*e* are left open. Pump 126 is then actuated to start a drain cycle. Because clamps 134*a*, 134*b* and 134*d* are closed while clamps 134*c* and 134*e* are open, pump 126 will drive spent dialysis fluid from patient 142 to drain bag 118. The heater of heater housing 106 may heat the dialysis fluid in heater bag 108 during the drain cycle. Once the drain cycle is complete, clamps 134*c* and 134*e* are closed. Filled drain bag 118 may be replaced by an empty drain bag 118.

Once the dialysis fluid in heater bag 108 is sufficiently heated, a patient fill cycle begins. Valves 132*a*, 132*b* and 132*c* are closed, while valve 132*d* remains open so that the only open air pathway from pump 124 is to the bladder of heater housing 106. Clamp 134*e* is opened to open a fluid pathway from heater bag 108 to patient 142. Air pump 124 is actuated to inflate the bladder of heater housing 106 in a controlled manner. Inflating the bladder drives heated dialysis fluid out of heater bag 108, through supply line 112, through supply connecting tube 150*d* and connector 120, through patient line 136, and into the peritoneal cavity of patient 142. The rate at which the bladder of heater housing 106 is inflated establishes the pressure and flow rate of the dialysis fluid through the fluid lines and into patient 142. To this end, pressure feedback from the patient line to control unit 104 may be provided to ensure that positive and negative pumping pressure limits are not exceeded. After a sufficient dwell time, a drain cycle is conducted. Clamp 134*d* is closed. Clamp 134*c* is opened, enabling a fluid pathway from patient 142 to drain bag 118. Pump 126 is then actuated to begin a drain cycle. Because clamps 134*a*, 134*b* and 134*d* are closed while clamps 134*c* and 134*e* are open, pump 126 pulls spent or used dialysis fluid from patient 142 and pushes same to drain bag 118. Once the drain cycle is complete, clamps 134*c* and 134*e* are closed. Filled drain bag 118 may be replaced by an empty drain bag 118.

Clamp 134*a* and clamp 134*d* are then opened to enable a fluid pathway from fluid supply bag 116*a* to heater bag 108. Valve 132*d* is closed and valve 132*a* is opened so that the only open air pathway from pump 124 is to nesting container 114*a*. Air pump 124 is then actuated to pump air into nesting container 114*a*. As the air pressure increases within nesting container 114*a*, dialysis fluid is driven out of fluid supply bag 116*a*, through fluid supply line 130*a*, through connecting tube 150*a*, connector 120 and connecting tube 150*d*, through heater fluid line 112, and into heater bag 108. The rate at which air is pumped into nesting container 114*a* controls the pressure and flow rate of the dialysis fluid through the fluid lines. After all or most of the dialysis fluid is transferred from fluid supply bag 116*a* to heater bag 108, the heater of heater housing 106 is actuated. Valves 132*a* and 134*a* may also be closed. In certain embodiments, dialysis fluid from fluid supply bag 116*a* may be transferred to heater bag 108 and heated simultaneously with the directly preceding drain cycle.

Once the dialysis fluid in heater bag 108 is sufficiently heated, a patient fill cycle begins. Valve 132*d* is opened to enable an air pathway to the bladder of heater housing 106. Clamp 134*e* is opened to enable a fluid pathway from heater bag 108 to patient 142. Air pump 124 is actuated to inflate the bladder of heater housing 106 in a controlled manner. Inflating the bladder drives heated dialysis fluid out of heater bag 108, through supply line 112, through supply connecting tube 150*d* and connector 120, through patient line 136, and into the peritoneal cavity of patient 142. The rate at which the bladder of heater housing 106 is inflated controls the pressure and flow rate of the dialysis fluid through the fluid lines and into patient 142. After a sufficient dwell time, a drain cycle is conducted. Here, clamp 134*d* is closed. Clamp 134*c* is opened, opening a fluid pathway from patient 142 to drain bag 118. Pump 126 is then actuated to start a drain cycle. Because clamps 134*a*, 134*b* and 134*d* are closed while clamps 134*c* and 134*e* are open, pump 126 will pull spent or used dialysis fluid from patient 142 and push same to drain bag 118. Once the drain cycle is complete, clamps

134*c* and 134*e* are closed. Filled drain bag 118 may be replaced by an empty drain bag 118.

Clamp 134*b* and clamp 134*d* are then opened to enable a fluid pathway from fluid supply bag 116*b* (e.g., the last-fill bag) to heater bag 108. Valve 132*d* is closed and valve 132*b* is opened so that the only open air pathway from pump 124 is to nesting container 114*b*. Air pump 124 is then actuated to pump air into nesting container 114*b*. As the air pressure increases within nesting container 114*b*, dialysis fluid is driven out of fluid supply bag 116*b*, through fluid supply line 130*b*, through connecting tube 150*b*, connector 120 and connecting tube 150*d*, through heater fluid line 112, and into heater bag 108. The rate at which air is pumped into nesting container 114*b* controls the pressure and flow rate of the dialysis fluid through the fluid lines. After all or most of the dialysis fluid is transferred from fluid supply bag 116*b* to heater bag 108, the heater of heater housing 106 is actuated. Valves 132*b* and 134*b* may also be closed. In certain embodiments, dialysis fluid from fluid supply bag 116*b* may be transferred to heater bag 108 and heated simultaneously with the directly preceding drain cycle.

Once the dialysis fluid in heater bag 108 is sufficiently heated, a patient fill cycle begins. Valve 132*d* is opened to enable an air pathway to the bladder of heater housing 106. Clamp 134*e* is opened to enable a fluid pathway from heater bag 108 to patient 142. Air pump 124 is actuated to inflate the bladder of heater housing 106 in a controlled manner. Inflating the bladder drives heated dialysis fluid out of heater bag 108, through supply line 112, through supply connecting tube 150*d* and connector 120, through patient line 136, and into the peritoneal cavity of patient 142. The rate at which the bladder of heater housing 106 is inflated controls the pressure and flow rate of the dialysis fluid through the fluid lines and into patient 142.

One having skill in the art will appreciate that control unit 104 may be programmed with many other sequences of performing the above-described drain, fill and dwell patient cycles for dialysis treatment. For example, heater bag 108 may begin in an empty state so that it must be filled with dialysis fluid from a fluid supply bag prior to a patient fill cycle. In another example, PD system 100 may include an additional fluid supply bag. In such examples, the control unit 104 is programmed with a sequence that includes directing the dialysis fluid from the additional fluid supply bag into heater bag 108, and thereafter into patient 142. Additionally, the order of some of the actions in the example sequence may be changed, certain actions may be executed simultaneously, one or more of the actions may be repeated, and some of the actions described may be optional.

In the above-described example sequence, nesting container 114*c* was not utilized. Instead, pump 126 (e.g., a peristaltic, membrane or gear pump) was utilized as the sole means to drive fluid from patient 142 to drain bag 118. In such examples, nesting container 114*c* and its associated components (e.g., pneumatic drain line 128*c*, drain connector 146*c*, connecting 148*c*, valve 132*c*) may not be included in PD system 100. In other aspects of the present disclosure, drain bag 118 and nesting container 114*c* may be particularly constructed to aid in driving fluid from patient 142 to drain bag 118 via air from air pump 124. In such aspects, pump 126 may remain in operable communication with drain fluid line 130*c* to aid in pulling used dialysis fluid of effluent from patient 142. In other instances, pump 124 may be removed.

Figure 5A:
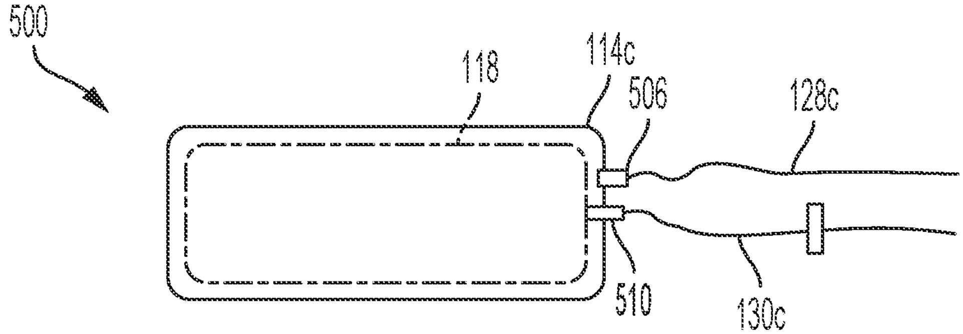
FIGS. 5A to 5C illustrate schematics of the components of a drain bag that is particularly constructed to aid in driving fluid from a patient to the drain bag via air from an air pump, according to an aspect of the present disclosure.
Figure 5B:
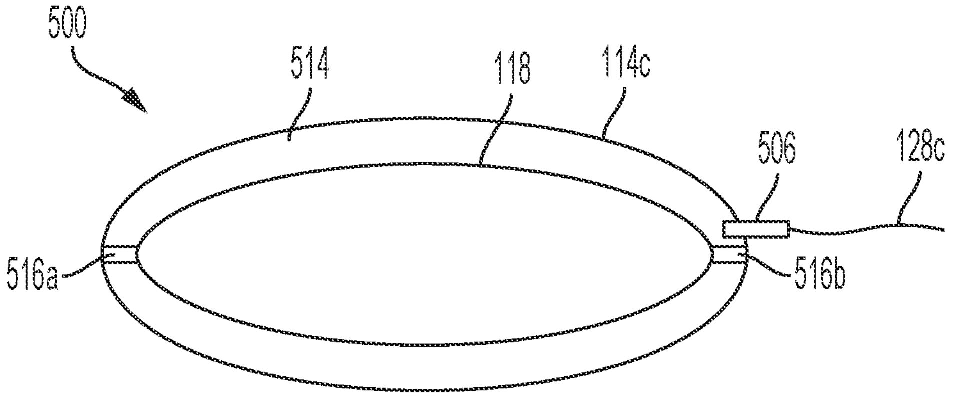
Figure 5C:
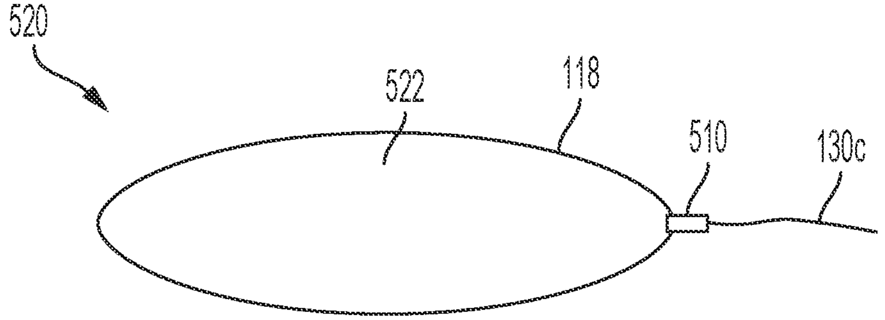

FIGS. 5A to 5C illustrate the components of an air-driven configuration 500 of the drain bag 118 and nesting container 114*c*. FIG. 5A illustrates a schematic top view of the example air-driven configuration 500 in a deflated state. Air-driven configuration 500 includes an outer component and an inner component. The outer component includes nesting container 114*c* in fluid communication with a pneumatic port 506 that is in fluid communication with a pneumatic drain line 128*c*. An airtight seal connects nesting container 114*c* and pneumatic port 506. Pneumatic drain line 128*c* is in fluid communication with air pump 124. The inner component includes drain bag 118 in fluid communication with a fluid port 510 that is in fluid communication with drain fluid line 130*c*. An airtight seal connects drain bag 118 and fluid port 510 and another airtight seal connects nesting container 114*c* and fluid port 510.

FIG. 5B illustrates a schematic cross-section of air-driven configuration 500 in a partially or fully expanded condition. Nesting container 114*c* is joined (e.g., fused) with drain bag 118 at multiple joining points 516*a*, 516*b*. In should be appreciated that the multiple joining points 516*a*, 516*b* may be at any position around the perimeter of drain bag 118. In at least one example, nesting container 114*c* is ultrasonically welded or solvent bonded to drain bag 118 at the multiple joining points 516*a*, 516*b*. As air is supplied to nesting container 114*c* through pneumatic drain line 128*c*, the air fills an interior 514 of nesting container 114*c*. As illustrated, interior 514 of nesting container 114*c* is exterior to drain bag 118 due to the airtight seal at the interface of fluid port 510 and drain bag 118 that does not allow air to enter drain bag 118.

FIG. 5C illustrates an interior component 520 of air-driven configuration 500. Interior component 520 includes drain bag 118 in fluid communication with fluid port 510 that is in fluid communication with fluid drain line 130*c*. An interior 522 of drain bag 118 is initially empty, though fills with fluid via fluid drain line 130*c* as dialysis fluid is pulled from patient 142.

Figure 6A:
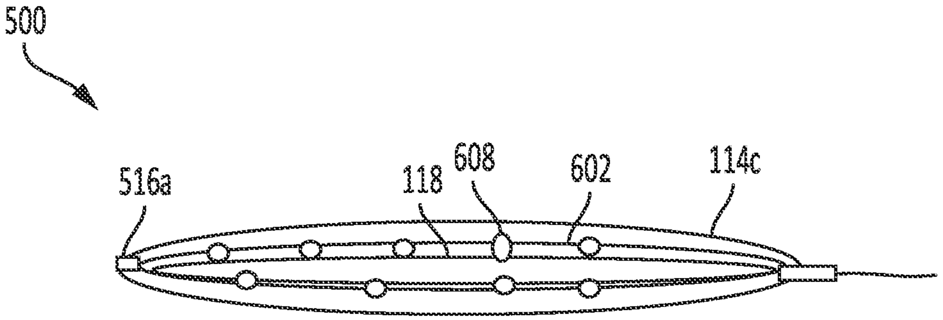
FIGS. 6A and 6B illustrate cross-sectional schematics of an air-powered drain bag to show the air driving mechanism driving fluid into the drain bag, according to an aspect of the present disclosure.
Figure 6B:
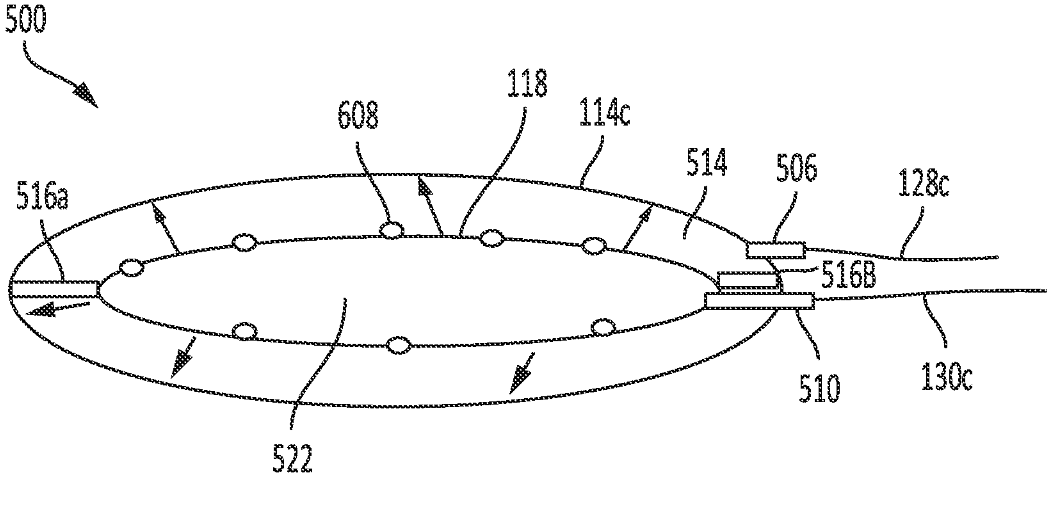

FIGS. 6A and 6B illustrate cross-sectional schematics of air-driven configuration 500 to show the air driving mechanism driving fluid into drain bag 118. FIG. 6A illustrates air-driven configuration 500 in a deflated condition. For illustrative purposes, multiple joining points 608 are shown joining (e.g., fusing) drain bag 118 to inner material 602 of nesting container 114*c*. It should be appreciated that only one joining point 608 is indicated in FIGS. 6A and 6B for clarity purposes. It should also be appreciated that the multiple joining points 608 may be at any position and take any shape around the exterior of drain bag 118. In at least one example, nesting container 114*c* is ultrasonically welded or solvent bonded to drain bag 118 at the multiple joining points 608. In one example, drain bag 118 may be fully joined to inner material 602 of nesting container 114*c*, rather than at multiple discrete points. In another example, drain bag 118 and nesting container 114*c* may be constructed as a single component rather than being joined.

Because of this construction of joining points 608, as nesting container 114*c* expands (e.g., fills with air), nesting container 114*c* pulls drain bag 118 open. Nesting container 114*c* may be constructed such that it transitions to a round shape after inflation. This is shown in FIG. 6B that illustrates air-driven drain bag 500 in a partially or fully expanded condition. As air enters interior 514 of nesting container 114*c* via pneumatic port 506, nesting container 114*c* expands outward in the direction of the illustrated arrows. Nesting container 114*c* expanding causes drain bag 118 to expand, which creates a vacuum force that pulls fluid into interior 522 of drain bag 118 via fluid port 510. The vacuum force is created because drain bag 118 is initially flat and devoid of any fluid, so as drain bag 118 is expanded, the volume created within drain bag 118 must be filled.

As described above, control unit 104 may be programmed to control the various components of PD system 100 to direct fluid flow and air flow. In instances in which drain bag 118 and nesting container 114*c* are constructed to aid in driving fluid from patient 142 to drain bag 118, control unit 104 may be programmed to activate air pump 124 to deliver air to nesting container 114*c* during a drain cycle. For instance, an example first drain cycle may include as follows, assuming that each clamp and valve in PD system 100 is initially open. Clamps 134*a*, 134*b* and 134*d* are closed. Clamps 134*c* and 134*e* are left open. Valves 132*a*, 132*b* and 132*d* are closed, while valve 132*c* remains open so that the only open air pathway from pump 124 is to nesting container 114*c*.

Air pump 124 is then actuated to start a drain cycle. Pump 126 may also be actuated in some instances. As air pump 124 provides air to nesting container 114*c* causing nesting container 114*c* to expand, nesting container 114*c* forces drain bag 118 open, creating a vacuum force. Because clamps 134*a*, 134*b* and 134*d* are closed while clamps 134*c* and 134*e* are open, the vacuum force will pull spend dialysis fluid from patient 142 to drain bag 118. If pump 126 is actuated, pump 126 will also help drive the spent dialysis fluid from patient 142 to drain bag 118. For example, the vacuum force may be insufficient, in some instances, to pull the entirety of the spent dialysis fluid from patient 142 and therefore pump 126 may help drive the fluid. In such instances, the vacuum force reduces the burden and wear on pump 126. The heater of heater housing 106 may heat the dialysis fluid in heater bag 108 during the drain cycle. Once the drain cycle is complete, clamps 134*c* and 134*e* are closed. Valve 132*c* may also be closed. Filled drain bag 118 may be replaced by an empty drain bag 118.

Without further elaboration, it is believed that one skilled in the art can use the preceding description to utilize the claimed inventions to their fullest extent. The examples and aspects disclosed herein are to be construed as merely illustrative and not a limitation of the scope of the present disclosure in any way. It will be apparent to those having skill in the art that changes may be made to the details of the above-described examples without departing from the underlying principles discussed. In other words, various modifications and improvements of the examples specifically disclosed in the description above are within the scope of the appended claims. For instance, any suitable combination of features of the various examples described is contemplated.

The invention is claimed as follows:

1. A peritoneal dialysis system comprising:
- a cycler including
  - an air pump, and
  - a heater housing including a heater and an expandable bladder in pneumatic communication with the air pump, wherein the heater housing is sized to receive a heater bag between a wall of the heater housing and the expandable bladder;
- a plurality of nesting containers configured for pneumatic communication with the air pump;
- a disposable set operable with the cycler and including the heater bag and a plurality of peritoneal dialysis fluid supply bags, each fluid supply bag positioned within one of the nesting containers; and
- a control unit programmed to control the air pump and the heater to pump heated dialysis fluid from the cycler.

2. The peritoneal dialysis system of claim 1, wherein the control unit is programmed to cause the air pump to pump air to a first nesting container to push dialysis fluid from a first fluid supply bag, the first fluid supply bag positioned within the first nesting container.

3. The peritoneal dialysis system of claim 1, which is configured such that each nesting container is inflatable with air from the air pump independently of the other nesting containers.

4. The peritoneal dialysis system of claim 1, which is configured such that inflating the expandable bladder with air drives fluid out of the heater bag when positioned in the heater housing.

5. The peritoneal dialysis system of claim 1, further comprising a plurality of valves positioned to selectively control, via the control unit, air flow from the air pump to the plurality of nesting containers.

6. The peritoneal dialysis system of claim 1, wherein the air pump is incorporated within the cycler.

7. The peritoneal dialysis system of claim 1, wherein the control unit is configured to control a rate of fluid flow from one of the fluid supply bags by controlling the air pump.

8. The peritoneal dialysis system of claim 1, which includes at least one pressure sensor in pressure feedback communication with the control unit, the control unit configured to use the pressure feedback to control the air pump so as not to exceed at least one patient pressure limit.

9. The peritoneal dialysis system of claim 1, wherein the disposable set further includes at least one of:
- the plurality of nesting containers,
- a drain bag,
- a supply line fluidly connected to each respective fluid supply bag,
- a heater line fluidly connected to the heater bag, or
- a drain line fluidly connected to the drain bag.

10. The peritoneal dialysis system of claim 9, wherein the drain bag is positioned within a drain nesting container, and wherein the drain bag is connected to the drain nesting container such that expansion of the drain nesting container causes expansion of the drain bag.

11. The peritoneal dialysis system of claim 10, which is configured such that pumping air to the drain nesting container creates a vacuum that pulls used dialysis fluid from a patient to the drain bag.

12. The peritoneal dialysis system of claim 10, wherein the drain bag is ultrasonically welded or solvent bonded to the drain nesting container.

13. The peritoneal dialysis system of claim 9, wherein the cycler further includes a drain pump positioned and arranged to deliver used dialysis fluid to the drain bag.

14. The peritoneal dialysis system of claim 1, wherein the cycler further includes a plurality of fluid line valves for selectively opening and occluding at least one of supply lines, a heater line or a drain line.

15. The peritoneal dialysis system of claim 1, which includes a plurality of pneumatic lines in pneumatic communication with the air pump, the expandable bladder and the nesting containers.

16. The peritoneal dialysis system of claim 15, wherein the pneumatic lines are reusable.

17. The peritoneal dialysis system of claim 1, wherein the plurality of nesting containers are reusable or disposable.

* * * * *